(12) United States Patent
Schultz et al.

(10) Patent No.: US 7,498,472 B2
(45) Date of Patent: *Mar. 3, 2009

(54) PROCESS FOR PRODUCING ETHYLBENZENE

(75) Inventors: Michael A. Schultz, Des Plaines, IL (US); Steven P. Lankton, Des Plaines, IL (US); Constante P. Tagamolila, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/752,525

(22) Filed: May 23, 2007

(65) Prior Publication Data

US 2008/0293985 A1 Nov. 27, 2008

(51) Int. Cl.
C07C 15/073 (2006.01)
C07C 2/64 (2006.01)
(52) U.S. Cl. .................. 585/323; 585/450; 585/470
(58) Field of Classification Search .......... 585/323, 585/450, 470
See application file for complete search history.

(56) References Cited

U.S. PATENT DOCUMENTS

| | | | |
|---|---|---|---|
| 2,471,134 A | 5/1949 | Wright ............... | 196/100 |
| 4,230,533 A | 10/1980 | Giroux ............... | 203/1 |
| 5,902,917 A | 5/1999 | Collins et al. ......... | 585/323 |
| 6,348,637 B1 | 2/2002 | Harris ............... | 585/820 |
| 6,395,950 B1 | 5/2002 | Rice ................ | 585/738 |
| 6,395,951 B1 | 5/2002 | Hamm .............. | 585/827 |
| 6,417,420 B1 | 7/2002 | Stewart et al. ........ | 585/323 |
| 6,479,720 B1 | 11/2002 | O'Brien et al. ........ | 585/448 |
| 6,483,002 B1 | 11/2002 | O'Brien ............. | 585/826 |
| 6,551,465 B1 | 4/2003 | Van Zile et al. ....... | 202/158 |
| 6,740,789 B1 | 5/2004 | Bozzano et al. ....... | 585/323 |
| 6,762,334 B1 | 7/2004 | Stewart et al. ........ | 585/323 |
| 6,927,314 B1 | 8/2005 | Schultz et al. ........ | 585/734 |

(Continued)

FOREIGN PATENT DOCUMENTS

EP 0 806 406 A1 11/1997

(Continued)

OTHER PUBLICATIONS

Schultz, Michael A. et al., "Reduce Costs with Dividing-Wall Columns" www.cepmagazine.org May 2002 pp. 64-71.

(Continued)

Primary Examiner—Thuan Dinh Dang
(74) Attorney, Agent, or Firm—Maryann Maas

(57) ABSTRACT

This ethylbenzene process involves contacting, in an alkylation zone, a first benzene recycle stream and an ethylene feed stream with an alkylation catalyst to form ethylbenzene. In a transalkylation zone, a polyethylbenzene recycle stream and a second benzene recycle stream are contacted with a transalkylation catalyst to form additional ethylbenzene. The effluents are passed into a dividing wall distillation column. An ethylbenzene stream is removed from an intermediate point of the dividing wall fractionation column; a first benzene recycle stream is removed from a first end and a flux oil stream is removed from a second end. A second benzene recycle stream is removed from an intermediate point located between the first end and the ethylbenzene stream. A polyethylbenzene stream is removed from an intermediate point of located between the second end and the ethylbenzene stream.

9 Claims, 1 Drawing Sheet

U.S. PATENT DOCUMENTS

| | | | |
|---|---|---|---|
| 6,979,394 B2 | 12/2005 | Bozzano et al. | 208/12 |
| 7,060,852 B2 | 6/2006 | Maas et al. | 562/94 |
| 2001/0052453 A1* | 12/2001 | Rust et al. | 202/158 |
| 2002/0017480 A1 | 2/2002 | Emmrich et al. | 208/313 |
| 2002/0019576 A1 | 2/2002 | Emmrich et al. | 585/866 |
| 2004/0011706 A1 | 1/2004 | Kaibel et al. | 208/347 |
| 2004/0020757 A1 | 2/2004 | Deibele et al. | 203/21 |
| 2004/0254411 A1 | 12/2004 | Steinbrenner et al. | 585/323 |
| 2006/0052630 A1 | 3/2006 | Narbeshuber et al. | 562/81 |
| 2006/0101852 A1 | 5/2006 | Porter | 62/620 |
| 2006/0178544 A1* | 8/2006 | Murray et al. | 585/467 |

FOREIGN PATENT DOCUMENTS

| | | |
|---|---|---|
| EP | 1 205 460 A1 | 5/2002 |
| WO | WO 03/051799 A1 | 6/2003 |

OTHER PUBLICATIONS

Rudd, Howard "Thermal coupling for energy efficiency" *Supplement to The Chemical Engineer* Aug. 27, 1992 pp. s14-s15.

Muralikrishna, K. et al., "Development of Dividing Wall Distillation Column Design Space for a Specified Separation" *Trans IChemE* vol. 80, Part A Mar. 2002 pp. 155-166.

* cited by examiner

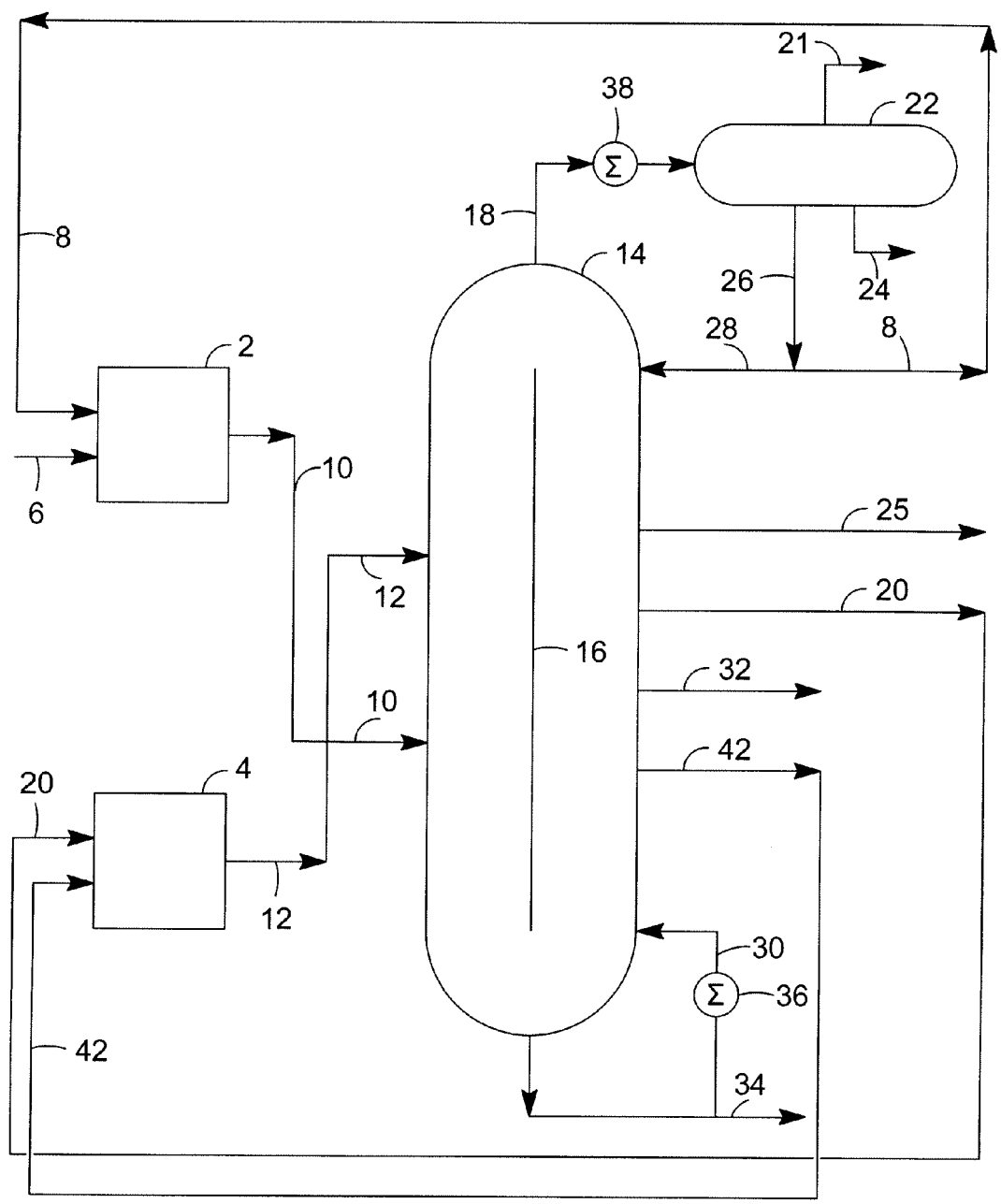

US 7,498,472 B2

PROCESS FOR PRODUCING ETHYLBENZENE

FIELD OF THE INVENTION

The invention is directed to a process for producing ethylbenzene where the product is separated using a dividing wall distillation column.

BACKGROUND OF THE INVENTION

Ethylbenzene is a valuable product that is used mainly for the manufacture of styrene monomer. Most ethylbenzene is produced by alkylation of benzene with ethylene. A byproduct also produced is polyethylbenzene. Therefore, ethylbenzene production processes contain two reaction sections, alkylation and transalkylation. The polyethylbenzenes produced from minor side reactions are recycled back to the transalkylation section and reacted with benzenes to produce more ethylbenzene. The alkylator and transalkylator effluents undergo separation operations to separate recycle benzene, ethylbenzene product, recycle polyethylbenzene and by-product streams using distillations. Traditionally three distillation columns are used. The first is typically a benzene column, used to recover excess benzene from the reactor effluents. The benzene column overhead, which is largely benzene, is typically recycled to the alkylator and transalkylator. The second distillation column is typically an ethylbenzene column used to recover the ethylbenzene product from the benzene column net bottoms. The ethylbenzene product is recovered as overhead, typically the net overhead, from the ethylbenzene column. The ethylbenzene product may be routed directly as feedstock to a styrene processes unit, or may be sent to storage. The third distillation column is usually a polyethylbenzene column used to recover recycle polyethylbenzene from the ethylbenzene column bottoms stream. Polyethylbenzene is recovered in the overhead of the polyethylbenzene column and is typically recycled to the transalkylator. The high boiling bottoms, flux oil, is usually cooled and sent to storage. Optionally, a fourth column, a light ends column, may be used to remove a small amount of light ends, light non-aromatics, and water from the recycle benzene stream.

The present invention provides an improvement over current process flow schemes by replacing the benzene column, the ethylbenzene column, and the polyethylbenzene columns with a single dividing wall column. The resulting advantages include a savings in the high pressure steam, a savings in condenser duty, a capital costs savings due to a reduction in equipment count and heat exchanger surface area, and a higher ethylbenzene recovery. Additional advantages include a reduction in plot space requirement, lower flare equipment costs, and less hydrocarbon inventory which relatively increases the inherent safety of the process unit.

The dividing wall or Petyluk configuration for fractionation columns was initially introduced some 50 years ago by Petyluk et al. A recent commercialization of a fractionation column employing this technique prompted more recent investigations as described in the article appearing at pages 14 of a *Supplement to The Chemical Engineer*, 27 Aug. 1992.

The use of dividing wall columns in the separation of hydrocarbons is also described in the patent literature. For instance, U.S. Pat. No. 2,471,134 issued to R. O. Wright describes the use of a dividing wall column in the separation of light hydrocarbons ranging from methane to butane. U.S. Pat. No. 4,230,533 issued to V. A. Giroux describes a control system for a dividing wall column and illustrates the use of the claimed invention in the separation of aromatics comprising benzene, toluene and orthoxylene.

Using a dividing wall column in the present invention provides significant advantages over ethylbenzene production processes that do not employ a dividing wall fractionation column, as is shown below.

SUMMARY OF THE INVENTION

An ethylbenzene generation process having a dividing wall fractionation zone has been developed. The process involves contacting, in an alkylation zone, a feed stream comprising at least ethylene and a first benzene recycle stream comprising at least benzene with an alklyation catalyst under alkylation conditions to convert at least a portion of the ethylene and benzene into ethylbenzene and form an alkylation zone effluent comprising benzene and ethylbenzene. Also, in a transalkylation zone, a polyethylbenzene recycle stream comprising at least polyethylbenzene and a second benzene recycle stream comprising at least benzene are contacted with a transalkylation catalyst under transalkylation conditions to convert at least a portion of the polyethylbenzene and benzene into ethylbenzene and form a transalkylation zone effluent comprising benzene and ethylbenzene. The alkylation zone effluent and the transalkylation zone effluent are passed into a dividing wall fractionation column which is operated at fractionation conditions. The dividing wall fractionation column is divided into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column. The two reactor effluents enter the column at one or more intermediate points of the first fractionation zone.

A stream comprising ethylbenzene is removed from an intermediate point of the second fractionation zone of the dividing wall fractionation column. A first benzene recycle stream is removed from a first end of the dividing wall fractionation column, and a flux oil stream is removed from a second end of the dividing wall fractionation column. The second benzene recycle stream is removed from an intermediate point of the second fractionation zone of the dividing wall fractionation column located between the first end of the column and intermediate point where the ethylbenzene stream is removed. A polyethylbenzene stream is removed from an intermediate point of the second fractionation zone of the dividing wall fractionation column located between the second end of the column and the intermediate point where the ethylbenzene stream is removed. Optionally a semi-dry benzene stream may be removed from an intermediate point of the second fractionation zone of the dividing wall fractionation column located between the first end of the column and the location where the second benzene recycle stream is removed from the dividing wall column.

BRIEF DESCRIPTION OF THE DRAWING

The FIGURE is a schematic illustration of one embodiment of the present invention. The FIGURE does not show a number of details for the process arrangement such as pumps, compressors, valves, stabilizers and recycle lines which are well known to those skilled in the art.

DETAILED DESCRIPTION OF THE INVENTION

Referring to the FIGURE, the process of the invention requires two reactors, an alkylation reactor 2, or alkylator, and a transalkylation reactor 4, or transalkylator. Ethylene and benzene feedstocks 6 and an excess of benzene 8 are introduced to alkylator 2. A typical ethylene feedstock may contain polymer grade ethylene (99.9 vol.-% min.) acetylene (10 ppm vol.-% max.), acetylene (1 ppm vol.-% max.), dienes (1 ppm vol.-% max.), propylene (25 ppm vol.-% max.), and C3 and heavier components (100 ppm vol.-% max.). A typical benzene feedstock may contain benzene (99.9 wt.-% min.) and toluene (0.05 wt.-% min.). Alkylation reactors may be operated in the vapor phase, liquid-phase or mixed-phase. It is preferred to operate the alkylation reactor in the liquid phase. At the lower temperatures of the liquid phase operation, xylene impurities are not produced and an ethylbenzene product of superior quality is produced. In one embodiment, the temperature of the alkylation reactor is selected from the range of 100° C. to 310° C. (212 to 590° F.) and the pressure is selected from the range of 800 to 5100 kPa (116 to 740 psig). In a more specific embodiment the temperature is in the range of 150 to 280° C. (303 to 536° F.) or 120 to 280° C. (248 to 536° C.) and the pressure is in the range of from about 1000 to 3900 kPa (145 to 570 psia). Alkylation reactor 2 contains an effective amount of alkylation catalyst. Suitable alkylation catalysts include solid acid catalysts and preferably a solid oxide zeolite. Examples are zeolite beta, zeolite X, zeolite Y, mordenite, faujasite, zeolite omega, UZM-8, MCM-22, MCM-36, MCM-49 and MCM-56. Alkylation reactors, operating conditions and catalysts are known in the art and not further discussed here.

In alkylation reactor 2, the benzene is alkylated with the ethylene to form ethylbenzene. Some polyethylbenzenes, which are mainly di- and tri-substituted ethylbenzenes, are also formed. Benzene is fed to the alkylator in excess so that virtually all the ethylene is reacted. Therefore, alkylation reactor effluent 10 contains primarily benzene, ethylbenzene and polyethylbenzenes.

Transalkylation reactor 4 is used to transalkylate benzene recycled in line 20 and the polyethylbenzene byproducts produced in the alkylation reactor and recycled in line 42 to form additional ethylbenzene. Suitable conditions and catalysts may be the same as described for the alkylation reactor. Examples of conditions include in one embodiment, the temperature is selected from the range of 170° C. to 270° C. (228 to 518° F.) and the pressure is selected from the range of 800 to 5100 kPa (116 to 740 psia). Transalkylation reactors, operating conditions and catalysts are known in the art and not further discussed here. The transalkylation effluent 12 from transalkylation reactor 4 contains primarily benzene, ethylbenzene and polyethylbenzene. Transalkylation effluent 12, for example, may contain from 30 to 70 wt.-% benzene, 10 to 50 wt.-% ethylbenzene, 5 to 30 wt.-% polyethylbenzene and from 0 to 5 wt-% flux oil. Suitable transalkylation catalysts include solid acid catalysts and preferably a solid oxide zeolite. Examples are zeolite X, zeolite Y, mordenite, faujasite, zeolite omega, MCM-22, MCM-36, MCM-49, MCM-56 and UZM-8. Transalkylation reactors, operating conditions, and catalysts are known in the art and not further discussed here.

Both alkylation effluent 10 and transalkylation effluent 12 are introduced to a dividing wall distillation column 14. Within the dividing wall distillation column are two parallel fractionation zones. A first fractionation zone occupies a large portion of the left-hand side of the mid-section of the distillation column. Note that the terms "left-hand" and "right-hand" are used herein as relative to the drawings. In actual practice the placement of the zones as to the left side or the right side of the column is not critical. This first fractionation zone is separated from a parallel second fractionation zone occupying the other half of the column cross section by a substantially fluid tight vertical wall 16. The vertical wall is not necessarily centered in the column and the two fractionation zones may differ in cross sectional area or shape. The vertical wall divides the vertical portion of the column into two parallel fractionation zones. The two zones are isolated from each other for the height of this wall, but communicate at both the top and bottom ends of the column. There is no direct vapor or liquid flow between the two fractionation zones through the dividing wall, but the upper end of the fractionation zone is open to the internal volume of the distillation column containing an undivided fractionation zone preferably having additional trays. Liquid may pass under the dividing wall at the bottom of the two fractionation sections although in some applications vapor flow may be restricted. Thus, vapor and liquid can freely move around the wall between the two portions of the column.

During operation, the components of both effluents are separated in the first fractionation zone with the more volatile compounds moving upward out of the left-hand first fractionation zone and emerging into the undividing upper portion of the distillation column. As with the first fractionation zone, the upper end of the right-hand second zone is in open communication with the upper section of the distillation column which may optionally contain additional fractionation trays extending across the entire column cross section.

The components of the effluent streams will separate according to boiling point or relative volatility, which is the main factor in determining their behavior in the distillation column. The component having a relatively low boiling point is the benzene from each of the effluents. The mid-range boiling component is the desired product, ethylbenzene. The components having relatively higher boiling points are the polyethylbenzenes, and the components having the highest boiling points are referred to as flux oils.

The transalkylation effluent 12 and the alkylation effluent 10 are introduced into a first vertical fractionation zone occupying a large portion of the left-hand side of the midsection of the distillation column. The effluents may be combined before being introduced, but advantages may be realized by introducing the effluents at different heights along the dividing wall distillation column. For example, the alkylation reactor effluent may contain a higher concentration of polyethylbenzene and therefore it may be advantageous to introduce the alkylation reactor effluent at a relatively lower height along the column as compared to the transalkylation reactor effluent. In one embodiment, the alkylation zone effluent is introduced into the dividing wall fractionation column at an intermediate height which is in between the height at which the transalkylation zone effluent is introduced and the first end of the of the column where the overhead is withdrawn.

The benzene present in the effluents is driven upwards in the first fractionation zone and enters the top section of the column where it is removed in overhead 18 and side draw 20. Benzene in overhead 18 is removed from the top of the dividing wall column and passed through an overhead condenser 38 to form liquid delivered to receiver 22. Receiver 22 may also have vent stream 21. A liquid phase stream of benzene 26 is removed from the receiver and dividing into a first portion 28 which is returned to the top of the dividing wall fractionation column as reflux and a second portion 8 which is recycled to the alkylation reactor 2 as the first benzene recycle stream. Benzene may also be removed from dividing wall column in stream 20 which is a side draw. Benzene stream 20 may be recycled to transalkylation reactor 4 as the second benzene recycle stream. Two benzene streams are withdrawn from the dividing wall fractionation column because the catalysts typically used in the alkylation reactor can tolerate some water present during the alkylation reaction, but the catalysts typically used in the transalkylation reactor are less tolerant of water. Therefore, the overhead contains benzene which may be saturated with water and is appropriate for the alkylation reactor, while the side draw contains dry benzene which is appropriate for the transalkylation reactor. As used herein the term "rich" is intended to indicate a concentration of the indicated compound or class of compounds greater than 50 and preferably greater than 75 mol percent.

The bottom of the dividing wall fractionation column 14 also comprises an undivided fractionation zone. This zone can receive liquid draining from both the first and second fractionation zones. This liquid is subjected to distillation which drives the ethylbenzene and polyethylbenzene upwards as vapor while concentrating the less volatile tars into a bottoms liquid 34 that is removed from dividing wall fractionation column 14. This separation is effected through the use of a reboiler 36 providing vapor to the bottom undivided fractionation zone. The product ethylbenzene stream 32 is withdrawn from the dividing wall fractionation column in a side draw from the right-hand side fractionation zone from the right-hand side fractionation zone. The byproduct polyethylbenzene stream 42 is withdrawn from the dividing wall fractionation column in a side draw. Polyethylbenzene stream 42 is withdrawn at a lower height of the column as compared to the ethylbenzene stream 32. The heavy aromatics stream 34 is removed as a bottoms stream from the dividing wall distillation column. A portion of stream 34 is passed through reboiler 36 and the remainder is recovered as net column bottoms, or flux oil stream.

Optionally, depending upon the applications, a semi dry benzene stream may be removed from the dividing wall fractionation column 14 in stream 25 as a side draw. Stream 25 is located at a height of dividing wall fractionation column between that of the benzene overhead 18 and second benzene recycle stream 20. It is most likely that either the set of stream 8 and 20 will be present or stream 25 will be present but not both. If the downstream use for the benzene can tolerate water such as that found in saturated benzene, stream 8 would be used. If the downstream use for the benzene cannot tolerate as much water, stream 20 would be used. If the downstream use for the benzene can tolerate more water than in stream 20, but less than in stream 8, the overhead may be operated under total reflux and the benzene taken as side draw 25 which would provide a semi dry benzene stream.

The dividing wall fractionation column may be further equipped with stabbed-in auxiliary reboilers and heat recovery exchangers located at strategic positions along the column. Examples of suitable locations for stabbed in reboilers include between the polyethylbenzene stream and the second end, and between the second benzene stream and the first end of the dividing wall distillation column. Such reboilers may be utilized to optimize the column diameter and energy consumption.

In a more specific embodiment of the invention, the undividing bottom section of the dividing wall fractionation column is depicted as separated from the two parallel fractionation zones by a gas flow control or gas trap out tray located just below the bottom of the wall. A slight gap at this point allows horizontal liquid flow between the parallel fractionation zones. This tray may have liquid sealed perforations allowing the normal downward flow of liquid, but its structure is such that the upward flow of vapor is at least greatly restricted or controlled. The tray may totally block the upward vapor flow. The use of this tray may provide a means to positively control the partition of the upward gas flow between the two fractionation zones, which is a prime means of controlling performance of the two zones. The vapor from the column bottoms is, therefore, preferably routed from the column via a line and split between two lines which feed the vapor to the bottom of the two parallel fractionation zones separately. The gas flow may be controlled by one or more flow control valves or by adjusting the relative liquid levels in the bottom of the two zones. This is described in some detail in U.S. Pat. No. 4,230,533.

It is believed that the separation performed in the present invention would compare favorably to that achieved using a conventional scheme employing a benzene column followed by an ethylbenzene column followed by a polyethylbenzene column. An investigation would most likely indicate that three conventional fractionation columns (the benzene column, the ethylbenzene column, and the polyethylbenzene column) could be replaced with the dividing wall column of the present invention to provide significant benefits and costs savings. It is expected that the reboiling duty may decrease as well as the total number of required stages. Additionally, one might expect there to be a small increase in ethylbenzene recovery which translates into a smaller loss of ethylbenzene product. Therefore, the present invention, through the use of the dividing wall column may reduce the capital costs as to the total number of trays as well as the utility costs as compared to a system of conventional fractionation columns. The total capital cost for the dividing wall column and its associated equipment, including heat exchangers, pumps, and receiving vessels, is expected to be less than the total for the columns it replaces, including the equipment associated with these columns. Several factors contribute to this cost reduction. First, as mentioned above, it is expected that the total reboiling duty may decrease as well as the total number of stages. The reduction in reboiling duty leads to a reduction in the size of the heat exchangers required for condensing and reboiling the column. In addition, the total pieces of equipment associated with a dividing fractionation wall column (including pumps, heat exchangers, and vessels) are fewer than the total required for the separate fractionation columns that it replaces. Fewer pieces of equipment for a more efficient separation will lead to a lower capital cost. The reduction in equipment count also leads to less tangible benefits. The total plot space requirement for the separation is reduced. In addition, the total inventory of hydrocarbon is reduced, thereby providing a relatively inherently safer process unit.

The invention claimed is:

1. An ethylbenzene generation process using a dividing wall fractionation zone, said process comprising:
 contacting, in an alkylation zone, at least ethylene, benzene, and a first benzene recycle stream comprising at least benzene with an alkylation catalyst under alkylation conditions to convert at least a portion of the ethylene and benzene into ethylbenzene and form an alkylation zone effluent comprising benzene and ethylbenzene;
 contacting, in a transalkylation zone, a polyethylbenzene recycle stream comprising at least polyethylbenzene and a second benzene recycle stream comprising at least benzene with a transalkylation catalyst under transalkylation conditions to convert at least a portion of the polyethylbenzene and benzene into ethylbenzene and form a transalkylation zone effluent comprising benzene and ethylbenzene;

passing the alkylation zone effluent and the transalkylation zone effluent into a dividing wall fractionation column operated at fractionation conditions and dividing into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the alkylation zone effluent and the transalkylation zone effluent entering the column at intermediate points of the first fractionation zone and wherein the transalkylation zone effluent is introduced into the dividing wall fractionation column at an intermediate height of the dividing wall fractionation column which is in between the first end of the dividing wall fractionation column and the intermediate height at which the alkylation zone effluent is introduced;

removing a stream comprising ethylbenzene from an intermediate point of the second fractionation zone of the dividing wall fractionation column;

removing the first benzene recycle stream from a first end of the dividing wall fractionation column and wherein the dividing wall fractionation column is operated so that the first recycle benzene stream is at a pressure ranging from 103 to 241 kPa (15 to 35 psia) and a temperature ranging from about 88 to 104° C. (190 to 220° F.);

removing a flux oil-rich stream from a second end of the dividing wall fractionation column;

removing the second benzene recycle stream from an intermediate point of the second fractionation zone of the dividing wall fractionation column located between the first end of the dividing wall fractionation column and the ethylbenzene stream; and removing a polyethylbenzene-rich stream from an intermediate point of the second fractionation zone of the dividing wall fractionation column located between the second end of the dividing wall fractionation column and the ethylbenzene stream.

2. The process of claim 1 wherein the alkylation zone is operated at a pressure in the range of from about 800 to about 5100 kPa (116 to 740 psia) and a temperature in the range of 100 to 310° C. (212 to 590° F.).

3. The process of claim 1 wherein the transalkylation zone is operated at a pressure in the range of 800 to 5100 kPa (116 to 740 psia) and a temperature in the range of 170 to 270° C. (338 to 518° F.).

4. The process of claim 1 further comprising passing the stream comprising ethylbenzene from an intermediate point of the second fractionation zone of the dividing wall fractionation column to a process for generating styrene monomer.

5. An ethylbenzene generation process using a dividing wall fractionation zone, said process comprising:

contacting, in an alkylation zone, at least ethylene, benzene, and a first benzene recycle stream comprising at least benzene with an alkylation catalyst under alkylation conditions to convert at least a portion of the ethylene and benzene into ethylbenzene and form an alkylation zone effluent comprising benzene and ethylbenzene;

contacting, in a transalkylation zone, a polyethylbenzene recycle stream comprising at least polyethylbenzene and a second benzene recycle stream comprising at least benzene with a transalkylation catalyst under transalkylation conditions to convert at least a portion of the polyethylbenzene and benzene into ethylbenzene and form a transalkylation zone effluent comprising benzene and ethylbenzene;

passing the alkylation zone effluent and the transalkylation zone effluent into a dividing wall fractionation column operated at fractionation conditions and dividing into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the alkylation zone effluent and the transalkylation zone effluent entering the column at intermediate points of the first fractionation zone and wherein the transalkylation zone effluent is introduced into the dividing wall fractionation column at an intermediate height of the dividing wall fractionation column which is in between the first end of the dividing wall fractionation column and the intermediate height at which the alkylation zone effluent is introduced;

removing a stream comprising ethylbenzene from an intermediate point of the second fractionation zone of the dividing wall fractionation column;

removing the first benzene recycle stream from a first end of the dividing wall fractionation column;

removing a flux oil-rich stream from a second end of the dividing wall fractionation column;

removing the second benzene recycle stream from an intermediate point of the second fractionation zone of the dividing wall fractionation column located between the first end of the dividing wall fractionation column and the ethylbenzene stream; and removing a polyethylbenzene-rich stream from an intermediate point of the second fractionation zone of the dividing wall fractionation column located between the second end of the dividing wall fractionation column and the ethylbenzene stream.

6. The process of claim 5 wherein the alkylation zone is operated at a pressure in the range of from about 800 to about 5100 kPa (116 to 740 psia) and a temperature in the range of 100 to 310° C. (212 to 590° F.).

7. The process of claim 5 wherein the transalkylation zone is operated at a pressure in the range of 800 to 5100 kPa (116 to 740 psia) and a temperature in the range of 170 to 270° C. (338 to 518° F.).

8. The process of claim 5 wherein the dividing wall fractionation column is operated so that the first recycle benzene stream is at a pressure ranging from 103 to 241 kPa (15 to 35 psia) and a temperature ranging from about 88 to 104° C. (190 to 220° F.).

9. The process of claim 5 further comprising passing the stream comprising ethylbenzene from an intermediate point of the second fractionation zone of the dividing wall fractionation column to a process for generating styrene monomer.

* * * * *